United States Patent [19]
Asakura et al.

[11] Patent Number: 5,955,469
[45] Date of Patent: Sep. 21, 1999

[54] PHARMACEUTICAL COMPOSITION

[75] Inventors: Sotoo Asakura, Kyoto; Michiyo Fukae, Osaka; Shigeo Nakanishi, Neyagawa; Yasuto Koyama, Itami; Youhei Kiyota, Ikeda, all of Japan

[73] Assignee: Fujisawa Pharmaceutical Co., Ltd., Osaka, Japan

[21] Appl. No.: 08/280,137

[22] Filed: Jul. 25, 1994

Related U.S. Application Data

[63] Continuation of application No. 07/786,782, Nov. 1, 1991, abandoned.

[30]    Foreign Application Priority Data

Feb. 11, 1990   [JP]   Japan ................................. 2-298135
Feb. 11, 1990   [JP]   Japan ................................. 2-298136

[51] Int. Cl.$^6$ .......................... A61K 31/44; A61K 31/40
[52] U.S. Cl. ................................. 514/291; 514/411
[58] Field of Search .............................. 514/291, 411

[56]     References Cited

U.S. PATENT DOCUMENTS

| | | | |
|---|---|---|---|
| 4,894,366 | 1/1990 | Okuhara et al. | 514/63 |
| 4,929,611 | 5/1990 | Okuhara et al. | 514/183 |
| 4,956,352 | 9/1990 | Okahara et al. | 514/63 |
| 5,011,844 | 4/1991 | Fehr | 514/291 |
| 5,260,301 | 11/1993 | Nakanishi et al. | |

FOREIGN PATENT DOCUMENTS

| | | |
|---|---|---|
| 0184162 | 6/1986 | European Pat. Off. . |
| 0315978 | 5/1989 | European Pat. Off. . |
| 0323042 | 7/1989 | European Pat. Off. . |
| 0428169 | 5/1991 | European Pat. Off. . |
| WO8905304 | 6/1989 | WIPO . |

OTHER PUBLICATIONS

Transplantation Proceedings, vol. XIX, No. 5, Suppl.6, Oct. 1987, pp. 17–22, T. Honbo, et al., "The Oral Dosage Form of FK–506".

Biopharmaceutics & Drug Disposition, vol. 5, 1984, pp. 141–151, C.T. Ueda, et al., "Apparent Dose–Dependent Oral Absorption of Cyclosporin A in Rats*".

Journal of Pharmaceutical Sciences, vol. 79, No. 3, Mar. 1990, pp. 216–219, S. Venkataram, et al., "Pharmacokinetics of Two Alternative Dosage Forms for Cyclosporine: Liposomes and Intra–Lipid".

Merck Index 11$^{th}$ Ed 1990 #A5.

Remington's Pharmaceutical Sciences 16$^{th}$ Ed (1980) Philadelphia College of Pharmacy & Science pp. 1518–1523.

*Primary Examiner*—Russell Travers
*Attorney, Agent, or Firm*—Oblon, Spivak, McClelland, Maier & Neustadt, P.C.

[57]     ABSTRACT

A pharmaceutical emulsion composition or solution composition in an organic solvent containing a compound represented by the following chemical formula and having immunosuppressive activity is disclosed:

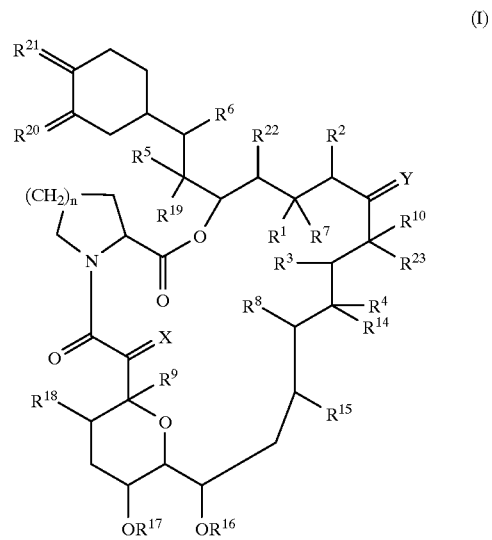

4 Claims, 1 Drawing Sheet

PHARMACEUTICAL COMPOSITION

This application is a continuation of application Ser. No. 07/786,782 filed Nov. 1, 1991, now abandoned.

BACKGROUND OF THE INVENTION

The present invention concerns a pharmaceutical composition containing a compound or a pharmaceutically acceptable salt thereof represented by the general formula (I) described later, that is noted as showing immunosupressive activity. More in particular, it relates to an emulsion composition which maintain a stable emulsified state in a physiological saline, glucose solution for injection, water, fruit juice or like other medium and, accordingly, can be applied by intravenous injection, intramuscular injection, local administration such as eye drop, as well as to various forms of administration including oral or rectal administration, or a pharmaceutically acceptable organic solvent solution composition that is in a stable liquid form by itself, shows less resistance upon administration as an oral formulation and has satisfactory absorbability from digestive tracts.

PRIOR ARTS

A compound represented by the following formula (I) and a pharmaceutically acceptable salt thereof has been known as a substance showing immunosupressive activity (refer to Japanese Patent Laid-Open Sho 61(1976)-148181 and European Patent Laid-Open No. 0323042), for which application uses in various medical fields have been expected, including transplantation of organs such as heart, liver, kidney, bone marrow, skin, cornea, lung, pancreas, small intestine, muscle, nerve, limb:

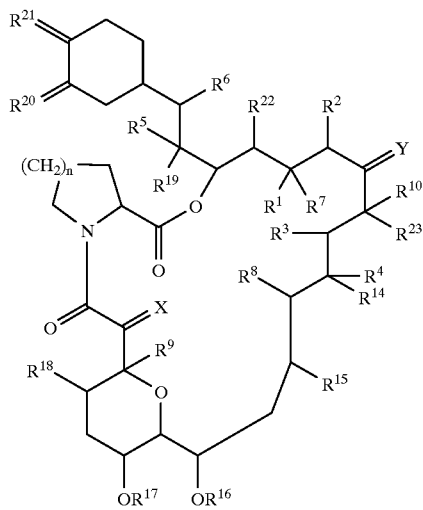

(I)

wherein each vicinal pair of $R^1$ and $R^2$, $R^3$ and $R^4$, $R^5$ and $R^6$ independently may
a) represently two vicinal hydrogen atoms, or
b) from a second bond between the vicinal carbon atoms to which they are attached;
in addition to the meanings above, $R^2$ may represent an alkyl group;
$R^7$ represents hydrogen, hydroxy group, protected hydroxy or alkyloxy group or, in conjunction with $R^1$, it may represent oxo group;
$R^8$ and $R^9$ independently represent hydrogen or hydroxy group;

$R^{10}$ represents hydrogen, alkyl group, alkyl group substituted by one or more hydroxyl groups, alkenyl group, alkenyl group substituted by one or more hydroxyl groups, or alkyl group substituted by oxo group;
X represents oxo group, (hydrogen atom, hydroxy group), (hydrogen atom, hydrogen atom) or —$CH_2O$—;
Y represents oxo group, (hydrogen atom, hydroxy group), (hydrogen atom, hydrogen atom) or N—$NR^{11}R^{12}$ or N—$OR^{13}$;
$R^{11}$, and $R^{12}$ independently represent hydrogen atom, alkyl, aryl or tosyl group;
$R^{13}$, $R^{14}$, $R^{15}$, $R^{16}$, $R^{17}$, $R^{18}$, $R^{19}$, $R^{22}$ and $R^{23}$ independently represent hydrogen atom or alkyl group;
$R^{20}$ and $R^{21}$ independently represent oxo group, or they may independently represent ($R^{20}$ a, hydrogen atom) and ($R^{21}$ a, hydrogen atom) respectively; $R^{20}$ a and $R^{21}$ a independently represent hydroxy group, alkyloxy group, or $OCH_2OCH_2CH_2OCH_3$ or $R^{21}$ a is protected hydroxy group;
in addition, $R^{20}$ a and $R^{21}$ a may together represent oxygen atoms in an epoxide ring; n is 1, 2 or 3;
in addition to the meanings above, Y, $R^{10}$ and $R^{23}$, together with the carbon atoms to which they are attached, may represent a 5- or 6-membered N-, S- or O-containing heterocyclic ring, which may be saturated or unsaturated, and which may be substituted by one or more groups selected from alkyl group, hydroxy group, alkyl group substituted by one or more hydroxyl groups, alkyloxy group benzyl and —$CH_2Se(C_6H_5)$.

Such compound (I) and its pharmaceutically acceptable salt are prepared in the same manner as the one described in the above-mentioned two patent applications. Particularly, the macrolides, which are produced by fermentation of *Streptomyces tsukubaensis* No.9993 (FERM BP-927) or *Streptomyces hygroscopicus* subsp. yakushimaensis No.7238 (FERM BP-928), are numbered FR-900506, FR-900520, FR-900523 and FR-900525.

SUMMARY OF THE INVENTION

The compound (I) and pharmaceutically acceptable salt thereof (hereinafter the term "compound (I)" is representatively used to show them) are less water soluble and, accordingly, when they are utilized as a pharmaceutical solution, it may be considered to solubilize them by using a generally used water soluble solubilizing agent (such as ethanol or polyethylene glycol).

However, a pharmaceutical solution prepared by the above-mentioned means may sometimes cause crystallization of the compound (I) when it is diluted with a body fluid in the applied portion, and it brings about a reduction of the bioavailability of the compound (I).

The present invention has been made in view of the foregoing situations and it is an object of the present invention to provide a pharmaceutical composition, in particular an emulsion composition or an organic solvent solution composition, which does not cause the crystallization of the compound (I) upon in contact with body fluid.

The pharmaceutical composition according to the present invention is in the form of a pharmaceutical composition the abovementioned compound (I) as the active ingredient, a pharmaceutically acceptable emulsifier and an oil phase ingredient, and particularly an O/W type emulsion or an organic solvent solution composition thereof.

DETAILED DESCRIPTION

Figure 1:
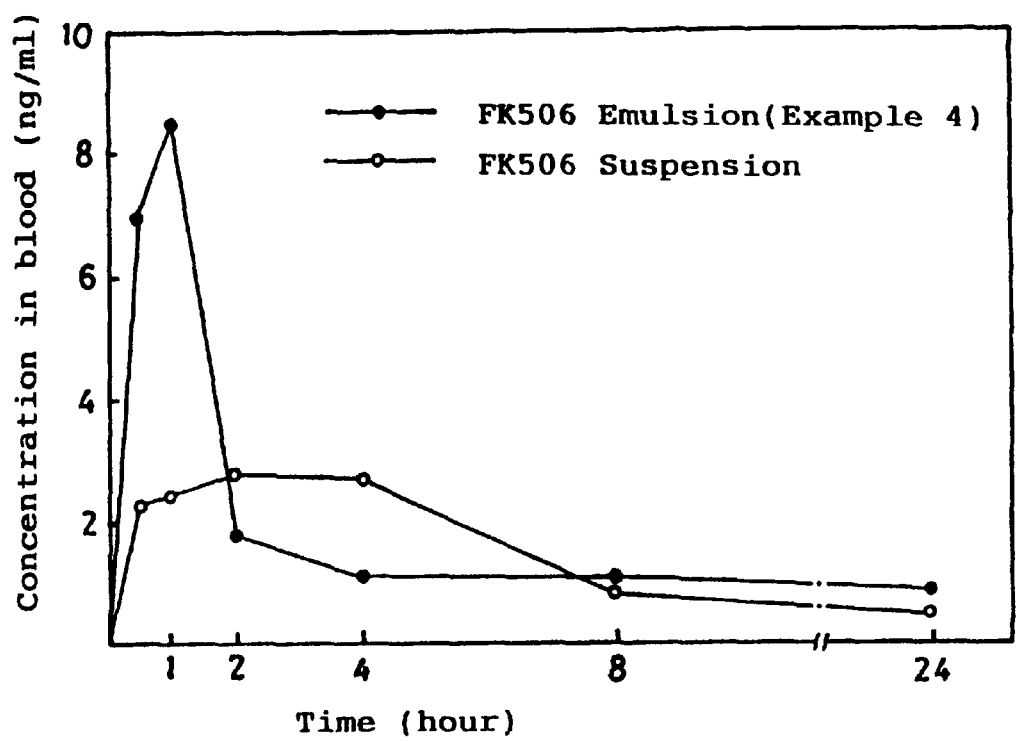
FIG. 1 is a graph illustrating the change of concentration in blood upon oral administration to rats evaluated in Example 5 to be described later.

Description will be made in details to the various definitions used in the general formula (I), suitable examples and illustrations of are explained in detail as follows.

The term "lower" as used in this specification means, unless otherwise indicated, a group having 1 to 6 carbon atoms.

Preferable examples of the "alkyl groups" are a straight or branched chain aliphatic hydrocarbon residue, for example, a lower alkyl group such as methyl, ethyl, propyl, isopropyl, butyl, isobutyl, pentyl, neopentyl, hexyl and the like.

Preferable examples of the "alkenyl groups" are a straight or branched chain aliphatic hydrocarbon residue having one double-bond, for example, lower alkenyl group such as vinyl, propenyl, butenyl, methylpropenyl, pentenyl, hexenyl and the like.

Preferable examples of the "aryl groups" include, for example, phenyl, tolyl, xylyl, cumenyl, mesityl and naphthyl and the like.

Preferable protective groups in the "protected hydroxy groups" are 1-(lower alkylthio)(lower) alkyl group such as a lower alkylthiomethyl group, for example, methylthiomethyl, ethylthiomethyl, propylthiomethyl, isopropylthiomethyl, butylthiomethyl, isobutylthiomethyl and hexylthiomethyl group, more preferably, $C_1$–$C_4$ alkylthiomethyl group, most preferably, methylthiomethyl group; trisubstituted silyl group such as a tri(lower)alkylsilyl,(for example, trimethylsilyl, triethylsilyl, tributylsilyl and tert-butyldimethylsilyl and tri-tert-butylsilyl), or lower alkyl-diarylsilyl, (for example, methyldiphenylsilyl, ethyldiphenylsilyl, propyldiphenylsilyl and, tert-butyldiphenylsilyl), more preferably tri($C_1$–$C_4$)alkylsilyl group and $C_1$–$C_4$ alkyldiphenylsilyl group, most preferably, tert-butyldimethylsilyl group and tert-butyldiphenylsilyl group; or an acyl group such as an aliphatic or aromatic acyl group derived from a carboxylic acid, sulfonic acid and carbamic acid, or an aliphatic acyl group substituted by an aromatic group.

Examples of the aliphatic acyl groups are a lower alkanoyl group optionally having one or more suitable substituents such as carboxy, for example, formyl, acetyl, propionyl, butyryl, isobutyryl, valeryl, isovaleryl, pivaloyl, hexanoyl, carboxyacetyl, carboxypropionyl, carboxybutyryl and carboxyhexanoyl; a cyclo(lower)alkoxy(lower)alkanoyl group optionally having one or more suitable substituents such as lower alkyl, for example, cyclopropyloxyacetyl, cyclobutyloxypropionyl, cycloheptyloxybutyryl, menthyloxyacetyl, menthyloxypropionyl, menthyloxybutyryl, menthyloxypentanoyl and menthyloxyhexanoyl; a camphorsulfonyl group or a lower alkylcarbamoyl group having one or more substituents such as carboxy or protected carboxy, for example, carboxy(lower)alkylcarbamoyl group, for example, carboxymethylcarbamoyl, carboxyethylcarbamoyl, carboxypropylcarbamoyl, carboxybutylcarbamoyl, carboxypentylcarbamoyl and carboxyhexylcarbamoyl, protected carboxy(lower)alkylcarbamoyl group such as tri(lower)alkylsilyl(lower)alkoxycarbonyl(lower)alkylcarbamoyl group, for example, trimethylsilylmethoxycarbonylethylcarbamoyol, trimethylsilylethoxycarbonylpropylcarbamoyl, triethylsilylethoxycarbonylpropylcarbamoyl, tertiary butyldimethylsilylethoxycarbonylpropylcarbamoyl and trimethylsilylpropoxycarbonylbutylcarbamoyl group and so on.

Examples of the aromatic acyl groups are an aroyl group optionally having one or more suitable substituents such as nitro, for example, benzoyl, toluoyl, xyloyl, naphthoyl, nitrobenzoyl, dinitrobenzoyl and nitronaphthoyl; or an arenesulfonyl group optionally having suitable substituents such as halogen, for example, benzenesulfonyl, toluenesulfonyl, xylenesulfonyl, naphthalenesulfonyl, fluorobenzenesulfonyl, chlorobenzenesulfonyl, bromobenzenesulfonyl and iodobenzenesulfonyl.

Examples of the aliphatic acyl groups substituted by aromatic group include ar(lower)alkanoyl group optionally having one or more substituents such as lower alkoxy or trihalo(lower)alkyl, for example, phenylacetyl, phenylpropionyl, phenylbutyryl, 2-trifluoromethyl-2-methoxy-2-phenylacetyl, 2-ethyl-2-trifluoromethyl-2-phenylacetyl and 2-trifluoromethyl-2-propoxy-2-phenylacetyl.

More preferable acyl groups among the aforesaid acyl groups are $C_1$–$C_4$ alkanoyl group optionally having carboxy, cyclo($C_5$–$C_6$)alkoxy($C_1$–$C_4$)alkanoyl group having two ($C_1$–$C_4$) alkyl at the cycloalkyl moiety, camphorsulfonyl group, carboxy($C_1$–$C_4$)alkylcarbamoyl group, tri($C_1$–$C_4$) alkylsilyl ($C_1$–$C_4$) alkoxycarbonyl($C_1$–$C_4$) alkylcarbamoyl group, benzoyl group optionally having one or two nitro groups, benzenesulfonyl group having halogen or phenyl ($C_1$–$C_4$)alkanoyl group having $C_1$–$C_4$ alkoxy and trihalo ($C_1$–$C_4$)alkyl group. Among these, the most preferable ones are, for example, acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the "heterocyclic groups" in the saturated or unsaturated 5- or 6-membered nitrogen, sulfur and/or oxygen containing ring include a pyrrolyl group or a tetrahydrofuryl group.

The pharmaceutically acceptable salts of the compound (I) include conventional non-toxic and pharmaceutically acceptable salts such as the salts with inorganic or organic bases, for example, an alkali metal salt such as sodium salt or potassium salt, an alkali earth metal salt such as calcium salt or magnesium salt, an ammonium salt or an amine salt such as triethylamine salt or N-benzyl-N-methylamine salt.

With regard to the compound (I) of the present invention, that there may be one or more conformers or stereo-isomeric pairs such as optical isomer and geometrical isomers due to the presence of asymetric carbon atom and double bond, and such conformers or isomers are also included within a scope of the present invention.

Description will now be made to the emulsifier used in the present invention.

As the emulsifier, pharmaceutically acceptable natural emulsifiers or synthetic emulsifiers are preferably used. Among them, various emulsifiers of animal or vegetable origin can be used as the natural emulsifier and typical examples thereof can include, for example, egg york lecithin, soybean lecithin or hydrogenation products thereof, phosphatidylcholine, phosphatidylserine, sphingomyelin, gum arabic and gelatine with no particular restriction. Further, any of cationic, anionic, nonionic or like other surface active agents can be used as the synthetic emulsifier. Nonionic surface active agent is particularly preferred and typical examples thereof can include castor oil type surface active agent, preferably, HCO (polyoxyethylene hardened castor oil) and, most preferably, HCO-60, HCO-50 and HCO-40 (trademark, prepared by Nikko Chemicals Co.respectively) in view of the long-time storability. In addition to the above, there can be also used polyoxyethylene sorbitan fatty acid ester derivative such as polysorbate 80, glycerin fatty acid ester derivative such as glycerin monocaprylate, and polyoxyethylene fatty acid ester derivative such as polyoxyethylene 40 monostearate, medium chained fatty acid mono (or di)glycerides (for example, fatty acid mono(or di) glycerides with 6 to 12 carbon atoms such as caprylic acid monoglyceride, caprylic acid diglyceride and capronic acid diglyceride) and polyoxyethylated glyceride such as polyoxyethylated oleic acid glyceride.

The emulsifier described above is used as a so-called primary emulsifier and optional use of an auxiliary emulsifier is also included within the scope of the present invention. There is no particular restriction at all on the kind of the auxiliary emulsifier and typical examples thereof can include, for example, cholesterol, agar, magnesium hydroxide, methylcellulose and pectin. In both of the primary emulsifier and the auxiliary emulsifier, each of the exemplified emulsifiers may be used in combination respectively.

Referring then to the oil phase ingredient used in the present invention, all of those pharmaceutically acceptable ingredients can be used and typical examples thereof can include, non-limitatively, vegetable oils (for example, soybean oil, sesame oil, cottonseed oil, olive oil, safflower oil, corn oil, rapeseed oil, peanut oil or the like), medium chained fatty acid triglycerides (for example, triglycerides of a fatty acid with 6 to 12 carbon atoms (for example, caprylic acid, capronic acid and lauric acid) such as Panasate 800, 810, 1000, 1200, manufactured by Nippon Yushi Co.), liquid hydrocarbons (for example, liquid paraffin, squalene and squalane), which may be used in combination.

The pharmaceutical composition according to the present invention comprises the ingredients as described above. In particular, a fine emulsion can be prepared as shown later in typical examples in a case of using egg york lecithin as the emulsifier and using the soybean oil as the oil phase ingredient, so that a highly stable pharmaceutical composition containing the compound (I) can be provided.

On the other hand, in a case of preparing an organic solvent solution composition as a pharmaceutical composition according to the present invention, any of organic solvents can be used so long as it can dissolve the compound (I) and is pharmaceutical acceptable, ethanol being most preferred. In this case, preferred emulsifier can include a polyoxyethylene hardened castor oil such as HCO-60 or a synthetic emulsifier such as polyoxyethylated glyceride (for example, polyoxyethylated oleic acid glyceride. And as the preferred oil phase ingredient, there can be mentioned medium chained fatty acid triglyceride. In this case, the compound (I) is dissolved into a mixed solvent comprising an organic solvent and a medium chained fatty acid triglyceride, or the compound (I) is at first dissolved into the organic solvent, to which the medium chained fatty acid triglyceride is added and, further, the synthetic emulsifier is added and mixed homogeneously. It is expected for the synthetic emulsifier that the medium chained fatty acid triglyceride is emulsified in contact with a digestive solution to improve the absorption for the compound (I). The medium chained fatty acid triglyceride has excellent solubility for the compound (I) as compared with the long chained fatty acid triglyceride (for example, olive oil), but it is immiscible with the synthetic emulsifier and can not provide a homogeneous pharmaceutical solution. In view of the above, the organic solvent, particularly preferably, ethanol is used together for allowing the medium chained fatty acid triglyceride and the synthetic emulsifier to be miscible homogeneously and reducing the viscosity of the entire solution to enhance the feeling of administration (easy usability) of the pharmaceutical composition.

In addition to the ingredients described above, a osmotic pressure controller may be used together corresponding to the portion of a living body to which the composition is applied and such an embodiment is also included within the scope of the present invention. Such an osmotic controller can include, for example, a sugar alcohol such as glycerine, sorbitol, inositol, xylytol and mannitol. Further, it is also possible to blend, as required, antiseptics (for example, benzalkonium chloride, various kinds of paraoxybenzoates, benzethonium chloride salt and chlorobutanol).

As has been described above, the composition of the present invention is a pharmaceutical composition comprising the compound (I), the emulsifier and the oil phase ingredient as the essential constituents and the content for each of the essential ingredients will now be explained. The content for the compound (I) is desirably set variously in accordance with the portion to which the composition is applied. The recommended content is from 0.05 to 50 mg/ml for intravenous injection, 1 to 50 mg/ml for intermuscular injection, 0.1 to 50 mg/ml for eye drop and 0.1 to 50 mg/ml for oral administration. The ingredient can be diluted with aqueous mediums, for example, water, physiological saline, glucose injection solution, fruits juice or milk in accordance with portion to which the composition is applied, so that the concentration is lowered than the level described above.

There is no particular restriction for the blending ratio of the oil phase ingredient in the pharmaceutical composition but it is preferred that the oil phase ingredient is blended in the form of the emulsion composition by from 5 to 50%(W/W), preferably, 5 to 20%(W/W). Further, the content of the emulsifier, in a case of a composition for injection or eye drops, is preferably from 0.5 to 50 parts by weight, more preferably, 1 to 30 parts by weight and, most preferably, 2 to 20 parts by weight based on 100 parts by weight of the oil phase ingredient used.

In a case of an oral composition, it is from 10 to 400 parts, preferably, from 50 to 200 parts by weight and, more preferably, from 80 to 120 parts by weight based on the 100 parts by weight of the oil phase ingredients.

Further, in a case of an organic solvent solution composition, the organic solvent is used by from 0.002 to 2 ml, preferably, from 0.01 to 1 ml and, particularly preferably, from 0.02 to 0.5 ml based on one mg of the compound (I).

The pharmaceutical composition can also be obtained when the compounds disclosed in the documents listed below are employed, such as EP-A-353678, Japanese Patent Application No. HEI 2(1990)-74330, PCT/GB90/01262, EP-A-413532, PCT/JP91/00314, British Patent Application No. 9012963.6, British Patent Application No. 9014136.7, British Application No. 9014681.2, British Patent Application No. 9014880.0, British Patent Application No. 9014881.8, British Patent Application No.9015098.8, British Patent Application No. 9016115.9, British Patent Application No. 9016693.5, EP-A-323865, EP-A-349061, EP-A-358508, EP-A-364031, EP-A-364032, EP-A-378317, EP-A-378320, EP-A-378321, EP-A-388153, EP-A-396399, EP-A-396400, EP-A-399579, EP-A-403242, EP-A-428365, EP-A-356399, GB 2225576 A, EP-A-402931 and EP-A-427680.

EXAMPLE

Example 1

As the compound (I), the following compound in which:
$R^1$, $R^2$, $R^8$, $R^{23}$=hydrogen
$R^7$, $R^9$=hydroxyl group $R^{10}$=allyl group $R^{14}, R^{15}, R^{16}, R^{17}, R^{18}, R^{19}, R^{22}$=methyl group $R^{20}=R^{20}a$, H ($R^{20}a$=methoxy)

$R^{21}=R^{21}a$, H ($R^{21}a$=hydroxyl group)

X, Y=oxygen n=2

$R^3, R^4$=form a second bond between the vicinal carbon atoms to which they are attached $R^5, R^6$=form a second bond between the vicinal carbon atoms to which they are attached, symbols represented by solid lines and the dotted lines=single bond, and being in a free form was used. The compound has an excellent immunosuppressive activity and is referred to hereinafter as FK506.

FK506 (0.5 g) was mixed with soybean oil (200 g) and egg york lecithin (24 g) and heated to about 80° C. to obtain a homogeneous solution.

Example 2

An aqueous 2.5% glycerine solution (1.6 liter) was added under heating at 70 to 80° C. to the homogenous solution obtained in Example 1 and emulsified by stirring for 30 min at 6000 rpm by using a TK homomixer (manufactured by Tokushu Kika Kogyo Co., JAPAN) while keeping a temperature at 70 to 80° C. Subsequently, it was emulsified while being kept at 75–80° C. by using Manton Gaurin Homogenizer (manufactured by Manton Gaurin Co., USA) under the conditions of a pressure at 4500 psi and number of pass of 10 times. After cooling the emulsion to a room temperature, distilled water was added to make the entire amount to 2 liter.

Example 3

After stirring FK506 (0.5 g) in 100 ml of a commercially available fat emulsion for intravenous injection (trade name, Intralipid 10%; manufactured by Ohtsuka Seiyaku) over one night under a room temperature, it was filtered by 0.45 µm filter made by Milipore Co. to prepare a fat emulsion for intravenous injection containing FK506 (concentration of FK506: 0.293 mg/ml).

Example 4

When a solution (comparataive example), suspension (comparative example) and emulsion (Example 3) were prepared and compared for rat transferability in rat eye, the results shown in Table 1 were obtained. As shown the table, the emulsion (Example 3) shows excellent transferability in rat eye and it is considered that the emulsion according to the present invention causes no deposition of the active ingredient when it is in contact with the body fluid. The conditions for the administration is 5 droplets by 10 µl, and the data in Table 1 show the concentration in each of tissues one hour after the administration (n=4, average value±standard deviation).

TABLE 1

| Preparation | Solution | Suspension (grain size: 6.5 µm) | Emulsion (fat emulsion for intravenous injection) |
|---|---|---|---|
| FK506 | 0.05 mg | 1 mg | 0.293 mg |
| HPMC | 3.5 | 3.5 | — |
| D-mannitol | — | — | — |
| Polysorbate 80 | 10 | — | — |
| Sodium hydrogen phosphate | 0.184 | 0.184 | — |
| Sodium dihydrogen phosphate | 15.47 | 15.47 | — |
| Phosphoric acid | 0.0032 | 0.0032 | — |
| Sodium chloride | 2.88 | 2.88 | — |
| Benzalconium chloride | 0.2 | 0.2 | — |
| Soybean oil | — | — | 100 |
| Egg york lecithin | — | — | 12 |
| Glycerin | — | — | 25 |
| Distilled water | to 1 ml | to 1 ml | to 1 ml |
| Transfer ability in rat eye [ng/wet (g)] | | | |
| Cornea | 192.9 ± 48.5 | 141.3 ± 21.7 | 762.8 ± 60.6 |
| Retina choroid | 2.6 ± 1.8 | 2.5 ± 0.7 | 26.2 ± 3.2 |
| Lens | n.d. | n.d. | 1.9± 0.7 |

Example 5

Each of the FK506 emulsion prepared in Example 3 and a solution prepared by suspending 30 mg of fine FK506 powder into 100 ml of physiological saline (FK506 suspension: grain size 10.3 µm) was orally administrated to each of rats and oral adsorption of FK506 was evaluated.

The absorption experiment was conducted by the following method.

Rats (male, SD series, 8 week age, 300 g body weight) abstained from fod in the previous day were fixed at its back and a sample was orally administrated by 1 mg/kg by means of a sonde (4 rats were used per one sample). Blood was collected (0.2 ml) from femeral aorta attached with a cannula at each of times (½, 1, 2, 4, 8 and 24 hr) and stored under refrigeration while adding 1% of heparin. After thawing them, the concentration of FK506 in the whole blood was determined by means of enzyme immunoassay.

The results are shown in FIG. 1. As shown in the figure, it has been found that, in case of the emulsion of the present invention, an absorption peak for FK506 appeared sooner and higher concentration in the blood was obtained as compared with the case of administrating the suspension.

Example 6

| | |
|---|---|
| FK506 | 2 mg |
| HCO-60 | 100 mg |
| Ethanol | 0.2 ml |
| Medium chained fatty acid triglyceride | to 1 ml |
| (Migriol 812 (trade name) manufactured by Huls AG) | |

Example 7

The store stability of the ethanol solution composition obtained in Example 6 was examined (Table 2).

TABLE 2

Form: Ethanol solution composition
Lot No.: Example 6

Preparation

| | |
|---|---|
| FK506 | 2 mg |
| HCO-60 | 100 mg |
| Anhydrous ethanol | 0.2 ml |
| Medium chained fat triglyceride | to 1 ml |

| Condition for storage | | Percent(%) of FK506 |
|---|---|---|
| Initial | | 100.0 (4.87) |
| 80° C. | 3 Days | 89.2 |
| | 5 Days | 84.3 |
| | 10 Days | 75.9 (4.42) |
| 60° C. | 10 Days | 95.3 |
| | 17 Days | 94.2 |
| | 1 Month | 88.8 (4.45) |
| 40° C. | 1 Month | 99.2 (4.77) |
| | 3 Months | 96.4 (4.54) |
| Activation energy (kcal/mol) | | 22.9 |
| $T_{90\%}$ forecast value at 25° C. | | 4.4 Years |

Values in brackets shows pH values for solution diluted by 5 times with water.

As shown in Table 2, it was confirmed that the long time storage of the ethanol solution composition obtained in Example 6 was possible.

Example 8

| | |
|---|---|
| FK506 | 2 mg |
| Polyoxyethylated oleic acid glyceride (Labrafil, M1944CS trade name, manufactured by Gatte fassé Co.) | 420 mg |
| Medium chained fatty acid glyceride | 400 mg |
| Ethanol | to 1 ml |

A composition containing each of the above-mentioned ingredients, capable of forming an emulsion upon use, was prepared by a conventional method.

Example 9

| | |
|---|---|
| FK506 | 1 mg |
| Caprylic acid monoglyceride | 0.2 ml |
| Medium chained fatty acid triglyceride | 0.6 ml |
| Ethanol | to 1 ml |

A composition containing each of the above-mentioned ingredients, capable of forming an emulsion upon use, was prepared by a conventional method.

EFFECT OF THE INVENTION

Since the pharmaceutical composition according to the present invention causes no crystallization of active ingredients when it is contacted with a body fluid, it has been confirmed that the composition shows excellent bioavailability and stability. Further, the pharmaceutical composition according to the present invention also has a merit that it gives comfortable taste to children and the dosage can be adjusted easily.

The pharmaceutical formulation according to the present invention, due to the pharmacological activity of the tricyclo compound (I), is useful for the treatment and prevention of immune-mediated diseases such as the resistance by transplantation of organs or tissue such as heart, kidney, liver, medulla ossium, skin, cornea, lung, pancreas, intestinum tenue, limb, muscle, nervous, etc.; graft-versus-host diseases by medulla ossium transplantation; autoimmune diseases such as rheumatoid arthritis, systemic lupus erythematosus, Hashimoto's thyroiditis, multiple sclerosis, myasthenia gravis, type I diabetes, and the like; and further infectious diseases caused by pathogenic microorganisms.

Further, the tricyclo compounds (I) are also useful for the treatment and the prophylaxis of inflammatory and hyperproliferative skin diseases and cutaneous manifestations of immunologically-mediated illnesses, such as psoriasis, atopical dermatitis, contact dermatitis and further eczematous dermatitises, seborrhoeis dermatitis, *Lichen planus*, Pemphigus, bullous Pemphigoid, *Epidermolysis bullosa*, urticaria, angioedemas, vasculitides, erythemas, cutaneous eosinophilias, *Lupus erythematosus*, acne and *Alopecia areata*;

various eye diseases such as autoimmune diseases and so on (e.g. keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' ophthalmopathy, Vogt-Koyanagi-Harada syndrome, sarcoidosis, etc.); reversible obstructive airways disease, which includes conditions such as asthma (e.g. bronchial asthma, allergic asthma, intrinsic asthma, extrinsic asthma and dust asthma), particularly chronic or inveterate asthma (e.g., late asthma and airway hyper-responsiveness), bronchitis and the like;

inflammation of mucosa and blood vessels such as gastric ulcers, vascular damage caused by ischemic diseases and thrombosis, ischemic bowel disease, inflammatory bowel disease, necrotizing enterocolitis, intestinal lesions associated with thermal burns, leukotriene $B_4$-mediated diseases;

intestinal inflammations/allergies such as Coeliac disease, proctitis, eosnophilic gastroenteritis, mastocytosis, Crohn's disease and ulcerative colitis; food related allergic diseases which have symptomatic manifestation remote from the gastro-intestinal tract, for example migraine, rhinitis and eczema; renal diseases such as interstitial nephritis, Goodpasture's syndrome, hemolytic-uremic syndrome and diabetic nephropathy;

nervous diseases such as multiple myositis, Guillain-Barré syndrome, Ménière's disease and radiculopathy; endocrine diseases such as hyperthyroidism and Basedow's disease;

hematic diseases such as pure red cell aplasia, aplastic anemia, hypoplastic anemia, idiopathic thrombocytopenic purpura, autoimmune hemolytic anemia, agranulocytosis and anerythroplasia;

bone diseases such as osteoporosis;

respiratory diseases such as sarcoidosis, fibroid lung and idiopathic interstitial pneumonia;

skin diseases such as dermatomyositis, leukoderma vulgaris, ichthyosis vulgaris, photoallergic sensitivity and cutaneous T cell lymphoma;

circulatory diseases such as arteriosclerosis, atherosclerosis, aortitis syndrome, polyarteritis nodosa and myocardosis;

collagen diseases such as scleroderma, Wegener's granuloma and Sjogren's syndrome;

adiposis;

eosinophilic fasciitis;

periodontal disease such as lesion of gingiva, periodontium, alveolar bone, substantia ossea dentis;

nephrotic syndrome such as glomerulonephritis;

male pattern alopecia or alopecia senilis;

muscular dystrophy;

Pyoderma and Sezary's syndrome;

active oxygen-mediated diseases, for example, organ injury such as ischemia-reperfusion injury of organs (e.g. heart, liver, kidney, digestive tract) which occurs on preservation, transplantation or ischemic diseases (e.g.thrombosis, cardiac infarction): intestinal diseases such as endotoxin-shock, pseudomembranous colitis, colitis caused by drug or radiation: renal diseases such as ischemic acute renal insufficiency, chronic renal insufficiency: pulmonary diseases such as toxinosis caused by lung-oxygen or drug (e.g. paracort, bleomycins), lung cancer, pulmonary emphysema: ocular diseases such as cataracta, siderosis, retinitis, pigmentosa, senile macular degeneration, vitreal scarring, corneal alkali burn: dermatitis such as erythema multiforme, linear IgA ballous dermatitis, cement dermatitis: and others such as gingvatis, periodontitis, sepsis, pancreatitis, diseases caused by environmental pollution (e.g. air pollution), aging, carcinogenis, metastasis of carcinoma, hypobaropathy; diseases caused by histamine or leukotriene C4 release; and so on.

And further, the tricyclo compounds (I) have liver regenerating activity and/or activities of stimulating hypertrophy and hyperplasia of hepatocytes. Therefore, they are useful for the treatment and prevention of hepatic diseases such as immunogenic diseases (e.g. chronic autoimmune liver diseases such as the group consisting of autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis, cirrhosis and hepatic failure such as fulminant hepatic failure, late-onset hepatic failure and "acute-on-chronic" liver failure (acute liver failure on chronic liver diseases).

And further, the tricyclo compounds (I) are useful for various diseases because of its useful pharmaceutical activity such as augmenting activity of chemotherapeutic effect, preventing or treating activity of cytomegalovirus infection, anti-inflammatory activity, and so on.

What is claimed is:

1. An injectable O/W emulsion composition containing 17-allyl-1,14-dihydroxy-12-(2-(4-hydroxy-3-methoxycyclohexyl)-1-methylvinyl)-23,25-dimethoxy-13,19,21,27-tetramethyl-11,28-dioxa-4-azatricyclo[22.3.1.0$^{4,9}$]octacos-18-ene-2,3,10,16-tetraone, egg yolk lecithin and soybean oil, in which egg yolk lecithin and soybean oil are in the ratio of 0.5–50:100 by weight.

2. The emulsion as defined in claim 1, wherein egg yolk lecithin and soybean oil are in the ratio of 2–20:100 by weight.

3. The emulsion as defined in claim 1, wherein glycerine is further included.

4. The emulsion as defined in claim 2, wherein glycerine is further included.

* * * * *

UNITED STATES PATENT AND TRADEMARK OFFICE
CERTIFICATE OF CORRECTION

PATENT NO. : 5,955,469

DATED : September 21, 1999

INVENTOR(S) : Sotoo ASAKURA, et al.

It is certified that error appears in the above-identified patent and that said Letters Patent is hereby corrected as shown below:

On the title page, item [30] should be:

--[30]  Foreign Application Priority Data
    Nov. 2, 1990  [JP]  Japan  ................ 2-298135
    Nov. 2, 1990  [JP]  Japan  ................ 2-298136--

Signed and Sealed this

First Day of August, 2000

*Attest:*

Q. TODD DICKINSON

*Attesting Officer*      *Director of Patents and Trademarks*